(12) United States Patent
Dhanak et al.

(10) Patent No.: US 6,420,424 B1
(45) Date of Patent: Jul. 16, 2002

(54) CCR-3 RECEPTOR ANTAGONISTS

(75) Inventors: Dashyant Dhanak, West Chester; Katherine L. Widdowson, King of Prussia; John R. White, Coatesville, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/674,208

(22) PCT Filed: Apr. 27, 1999

(86) PCT No.: PCT/US99/08950

§ 371 (c)(1),
(2), (4) Date: Oct. 27, 2000

(87) PCT Pub. No.: WO99/55330

PCT Pub. Date: Nov. 4, 1999

Related U.S. Application Data

(60) Provisional application No. 60/083,229, filed on Apr. 27, 1998.

(51) Int. Cl.$^7$ .............................................. A61R 31/24
(52) U.S. Cl. ...................... 514/538; 514/539; 514/541
(58) Field of Search ................................. 514/538, 539, 514/541

(56) References Cited

U.S. PATENT DOCUMENTS

| | | |
|---|---|---|
| 5,684,032 A | 11/1997 | Elliott et al. |
| 5,919,776 A | 7/1999 | Hagmann et al. |
| 5,919,790 A | 7/1999 | Allen et al. |

*Primary Examiner*—James H. Reamer
(74) *Attorney, Agent, or Firm*—Soma G. Simon; William T. King; Charles M. Kinzig

(57) ABSTRACT

Phenylalanine sulfonamide derivatives and their use as CCR-3 receptor antagonist.

9 Claims, No Drawings

CCR-3 RECEPTOR ANTAGONISTS

This application is a 371 of PCT99/08950, filed Apr. 27, 1991 which claims benefit of provisional application 60/083,229, filed Apr. 27, 1998.

FIELD OF THE INVENTION

The present invention relates to the use of phenylalanine amide derivatives, and pharmaceutical compositions containing these compounds as Chemokine/CCR-3 receptor antagonists.

Chemokines are a superfamily of small secreted proteins. There are approximately 30 distinct chemokines known with many others being characterized. See Oppenheim et al., Properties of the Novel Proinflammatory Supergene "Intercrine" Cytokine Family, *Ann. Rev. Immun.*, 9, 617–648 (1991); and Baggiolini, et al., Interleukin-8 and Related Chemotactic Cytokines-CXC and CC Chemokines, *Adv. Immun.*, 55, 97–179 (1994). The properties of the chemokines suggest that they are essential for leukocyte trafficking and inflammatory processes, and are thus important components in a number of disease states. See Kita et al., Chemokines Active on Eosinophils: Potential Roles in Allergic Inflammation, *J. Exp. Med.*, 183, 2421–2426 (1996); Strieter, et al., "The Good, the Bad and the Ugly" The Role of Chemokines in Models of Human Diseases, *J. Immun.*, 157, 3583–3586 (1996); and Baggiolini, Eotaxin: a VIC (Very Important Chemokine) of Allergic Inflammation, *J. Clin. Invest.*, 97,587 (1996).

Chemokines mediate their effects via interactions with 7TM-G-protein coupled receptors on the surface of immune and inflammatory cells. Eosinophils are proinflammatory granulocytes that play a major role in allergic diseases, such as bronchial asthma, allergic rhinitis, pruritis and atopic dermatitis. Upon activation, eosinophils release lipid mediators, cytotoxic proteins, oxygen metabolites and cytokines, all of which have the potential to produce pathophysiology. Numerous studies have demonstrated the presence of eosinophils or eosinophil-specific products in inflamed tissues in human diseases.

The mechanisms responsible for the selective infiltration of eosinophils in allergic diseases have yet to be clarified. Recently, a CC chemokine, eotaxin, was identified in guinea pigs and demonstrated to be present in a guinea pig model of allergic airway inflammation. See Jose, et al., Eotaxin: A Potent Eosinophil Chemoattractant Cytokine Detected in Guinea Pig Model of Allergic Airways Inflammation, *J. Exp. Med.*, 179, 881–887 (1994); and Jose, et al., Eotaxin: Cloning of an Eosinophil Chemoattractant Cytokine and Increased mRNA Expression in Allergen-challenged Guinea-pig Lungs, *Biochem. Biophys. Res. Comm.*, 205, 788–794 (1994). The human homologue of Guinea-pig eotaxin has been expressed and has been shown to induce eosinophil infiltration when injected into the skin of the rhesus monkey. See Ponath, et al., Cloning of the Human Eosinophil Chemoattractant, Eotaxin: Expression, Receptor Binding, and Functional Properties Suggest a Mechanism for Selective Recruitment of Eosinophils, *J. Clin. Invest.*, 97, 604–612 (1996).

The cloning, expression and characterization of a novel C—C chemokine receptor, designated CCR-3 from peripheral blood eosinophils and from an eosinophil cDNA library have also been reported. See Kitaura, et al., Molecular Cloning of Human Eotaxin, an Eosinophil-selective CC Chemokine, and Identification of a Specific Eosinophil Eotaxin Receptor, CC Chemokine Receptor 3, *J. Biol. Chem.*, 271, 7725–7730 (1996); Ahuja, et al., Cloning and Functional Expression of a Human Eosinophil CC Chemokine Receptor, *J. Biol. Chem.*, 270, 16491–16494 (1995); Daugherty, et al., Cloning, Expression and Characterization of the Human Eosinophil Eotaxin Receptor, *J. Exp. Med.* 183,,2349–2354 (1996); and Ponath, et al., Molecular Cloning and Characterization of a Human Eotaxin Receptor Expressed Selectively on Eosinophils, *J. Exp. Med.*, 183, 2437–2448 (1996).

Eotaxin, MCP-4 and, to a lesser extent, RANTES and MCP-3 activate this receptor. The CCR-3 receptor is expressed at high levels on eosinophils; typically 40,000–400,000 receptors per cell are present. This is 10–100 fold more than the other chemokine receptor (CCR-1) expressed in eosinophils. Monoclonal antibodies raised to the CCR-3 receptor demonstrate that the receptor is primarily restricted to eosinophils and a subset of Th2 T-cells. This restricted expression on eosinophils and T-cells may be responsible for the selective recruitment of eosinophils and Th2 T-cells in allergic inflammation. Additionally, CCR-3 is potently activated by eotaxin 1, eotaxin and MCP-4. See Stellato et al., Production of the Novel CC Chemokine MCP-4 by Airway Cells and Comparison of Its Biological Activity to other CC-Chemokines. *J. Clin. Invest.* 99, 92–936 (1997). In contrast, other known chemokines appear to activate more than one chemokine receptor, e.g. RANTES binds to CCR-1, CCR-3, CCR-4 and CCR-5 receptors.

The foregoing research advances have provided the impetus to investigate the inhibition of eosinophil-specific chemokines in order to examine its role in blocking cellular infiltration in inflamed tissues. CCR-3 receptor antagonists thus offer a unique approach toward decreasing the pathophysiology associated with allergic diseases. Antagonism of this receptor may be useful in the treatment of allergic disorders, including but not limited to bronchial asthma, allergic rhinitis, eczema, nasal polyposis, conjunctivitis, atopic dermatitis, inflammatory bowel disorder and pruritis.

SUMMARY OF THE INVENTION

The present invention involves phenylalanine amide derivatives represented by Formula (1) hereinbelow and their use as CCR-3 receptor antagonists which is useful in the treatment of a variety of diseases associated with allergic disorders, including but not limited to bronchial asthma, allergic rhinitis, nasal polyposis, atopic dermatitis and pruritis.

The present invention further provides methods for antagonizing CCR-3 receptors in an animal, including humans, which comprises administering to a subject in need of treatment an effective amount of a compound of Formula (I) or (II) as indicated hereinbelow.

DETAILED DESCRIPTION OF THE INVENTION

The compounds useful in the present methods are selected from Formula (I) or (II) hereinbelow:

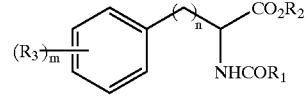

Formula (I)

wherein
n is an integer from 0 to 3;
$R_1$ is selected from the group consisting of N-carbobenzoxy-L-Phe, N-Ac-L-Pro, $C_{1-6}$ alkyl, $OC_{1-4}$ alkyl, aryl and heteroaryl, unsubstituted, monosubstituted, disubstituted or trisubstituted, with any substituents being independently selected from the group consisting of $C_{1-4}$ alkyl, COaryl, $OCH_2O$, $NO_2$, Cl and $OCH_3$.

$R_2$ represents $C_{1-4}$ alkyl or benzyl;

m is an integer from 1 to 3: and $R_3$ is independently selected from the group consisting of OH, $OC_{1-4}$ alkyl, $NO_2$, $NH_2$, halo, naphthyl, and OCOphenyl; or

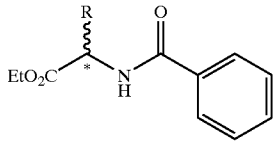

Formula (II)

wherein R represents indolylmethyl, phenyl or $(CH_2)_2$phenyl.

Preferably, in Formula(I), n represents 1

Preferably, in Formula(I), at the $R_1$ position, alkyl represents $cC_6H_{11}$ or n-Bu. Preferably, O-alkyl represents O-t-Bu. Preferably, aryl represents phenyl or naphthyl. Preferably, heteroaryl represents thienyl, furyl, pyridyl, or quinolinyl.

Preferably, substituents at $R_1$ are independently selected from the group consisting of $C_{1-2}$ alkyl, CO-phenyl, $OCH_2O$, $NO_2$, Cl, OH, and $OCH_3$.

Preferably, at $R_2$, alkyl moieties are methyl or ethyl.

A preferred halo moiety at $R_3$ is iodo.

Preferably, in Formula (II), the carbon atom marked with the asterix (*) represents an S configuration.

Preferred compounds of the present invention include:

(S)-Ethyl-2-(1-napthoylamino)3-(4-nitrophenyl)propionate,
(S)-Isopropyl-2-(1-napthoylamino)3-(4-nitrophenyl) propionate,
(S)-Methyl-2-(1-napthoylamino)3-(4-nitrophenyl) propionate,
(S)-Benzyl-2-(1-napthoylamino)3-(4-nitrophenyl) propionate,
(S)Ethyl-2-(1-napthoylamino)3-(4-chlorophenyl) propionate,
(S)-Ethyl-2-benzoylamino-3-(4-hydroxyphenyl)propionate,
(S,S)-Ethyl-2-(2-benzyloxycarbonylamino-3-phenylpropionylamino)-3-(4-hydroxyphenyl)propionate,
(S,S)-Ethyl-2-(N-acetylpyrrolidine-2-benzoylamino)-3-(4-hydroxy-phenyl)propionate,
(S)-Ethyl-2-cyclohexanylamino-3-(4-hydroxyphenyl) propionate,
(S)-Ethyl-2-(3,3-diphenylpropionylamino)-3-(4-hydroxyphenyl)propionate,
(S)-Ethyl-2-(3-phenylpropionylamino)-3-(4-hydroxyphenyl)propionate,
(S)-Ethyl-2-[2-(2-naphthyl)acetylamino)-3-(4-hydroxyphenyl)propionate,
(S)-Ethyl-2-(4-phenylbutyrylamino)-3-(4-hydroxyphenyl) propionate,
(S)-Ethyl-2-pentanylamino-3-(4-hydroxyphenyl) propionate,
(S)-Ethyl-2-pentanylamino-3-(4-hydroxyphenyl) propionate,
(S)-Ethyl-2-(4-benzoylbenzoylamino)-3-(4-hydroxyphenyl) propionate,
(S)-Ethyl-2-(2-furanyl)amino-3-(4-hydroxyphenyl) propionate,
(S)-Ethyl-2-(1-naphthoylamino)-3-(4-hydroxyphenyl) propionate,
(S)-Ethyl-2-(5-hydroxyindonyl)amino-3-(4-hydroxyphenyl) propionate,
(S)-Ethyl-2-piperonylamino-3-(4-hydroxyphenyl) propionate,
(S)-Ethyl-2-picolinylamino-3-(4-hydroxyphenyl) propionate,
(S)-Ethyl-2-(3-nitro-4-chlorobenzoylamino)-3-(4-hydroxyphenyl)propionate,
(S)-Ethyl-2-(3-hydroxy-4-nitrobenzoylamino)-3-(4-hydroxyphenyl)propionate,
(S)-Ethyl-2-(8-quinolinylamino)-3-(4-hydroxyphenyl) propionate,
(S)-Ethyl-2-benzoylamino-3-phenylpropionate,
(S)-Methyl-2-benzoylamino-3-(4-hydroxyphenyl) propionate,
(S)-Benzyl-2-benzoylamino-3-(4-hydroxyphenyl) propionate,
(S)-Ethyl-2-benzoylamino-3-(4-methoxyphenyl)propionate,
(S)-Ethyl-2-tert-butyloxycarbonylamino-3-(4-nitrophenyl) propionate,
(S)-Ethyl-2-tert-butyloxycarbonylamino-3-(4-aminophenyl) propionate,
(S)-Ethyl-2-benzoylamino-3-(3,5-diiodo-4-hydroxyphenyl) propionate,
(S)-Ethyl-2-carboxybenzoylamino-3-(4-hydroxyphenyl) propionate,
(S)-Ethyl-2-benzoylamino-3-(1-naphthyl)propionate,
(±)-Ethyl-2-benzolyamino-3-[3-(benzoyloxy)phenyl] propionate,
(±)-Ethyl-2-benzoylamino-3-(3-hydroxyphenyl)propionate,
(R,S)-Ethyl-2-benzoylamino-3-(2-hydroxylphenyl) propionate,
(S)-Ethyl-2-benzoylamino-3-(4-aminophenyl)propionate,
(S)-Ethyl-2-benzoylamino-3-(4-nitrophenyl)propionate,
(S)-Ethyl-2-(2-phenylacetylamino)-3-(4-hydroxyphenyl) propionate,
(S)-Ethyl-2-benzoylamino-3-(3-indoyl)propionate,
(±)-Ethyl-2-(benzoylamino)-2-phenylacetate, and
(±)-Ethyl-2-(benzoylamino)-4-phenylbutyrate.

More preferred compounds of the present invention include:

(S)-Ethyl-2-(1-napthoylamino)3-(4-nitrophenyl)propionate,
(S)-Ethyl-2-benzoylamino-3-(4-hydroxyphenyl)propionate,
(S)-Ethyl-2-cyclohexanylamino-3-(4-hydroxyphenyl) propionate,
(S)-Ethyl-2-(1-naphthoylamino)-3-(4-hydroxyphenyl) propionate,
(S)-Benzyl-2-benzoylamino-3-(4-hydroxyphenyl) propionate,
(S)-Ethyl-2-benzoylamino-3-(4-methoxyphenyl)propionate,
(S)-Ethyl-2-benzoylamino-3-(1-naphthyl)propionate,
(±)-Ethyl-2-benzolyamino-3-[3-(benzoyloxy)phenyl] propionate,
(±)-Ethyl-2-benzoylamino-3-(3-hydroxyphenyl)propionate,
(R,S)-Ethyl-2-benzoylamino-3-(2-hydroxylphenyl) propionate,
(S)-Ethyl-2-benzoylamino-3-(4-nitrophenyl)propionate,
(±)-Ethyl-2-(benzoylamino)-2-phenylacetate, and
(±)-Ethyl-2-(benzoylamino)-4-phenylbutyrate.

The most preferred compounds useful in the present invention include:

(S)-Ethyl-2-(1-naphthoylamino)-3-(4hydroxyphenyl) propionate,
(S)-Ethyl-2-(1-napthoylamino)3-(4-nitrophenyl)propionate, and
(S)-Ethyl-2-benzoylamino-3-(4-nitrophenyl)propionate.

Also included in the present invention are pharmaceutically acceptable salt complexes. Preferred are the ethylene diamine, sodium, potassium, calcium and ethanolamine salts. The compounds of the present invention may contain one or more asymmetric carbon atoms and may exist in racemic and optically active forms. All of these compounds and diastereomers are contemplated to be within the scope of the present invention.

The present compounds can be prepared by the using the overall strategies provided hereinbelow. Such strategies are readily found in the art. See e.g. Comprehensive Organic Transformations, R. C. Larock, VCH Publishers, 1989(and references therein); and Organic chemistry, Vol. 1; I. L. Finar, Longman Group, 1973.

The present compounds are readily prepared by conventional acylation methods (for example as used in peptide synthesis) and well known to those skilled in the art and are exemplified in Scheme I below:

SCHEME 1

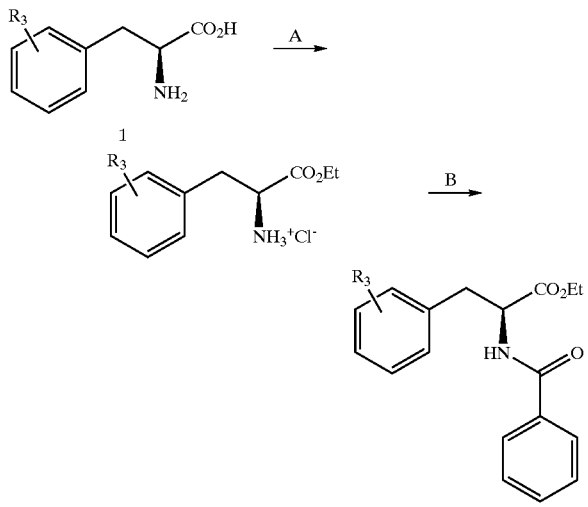

A: EtOH, HCl, reflux; B: PhCO$_2$H, EDCI, HOBt, NMM, HOBt or PHCOCl, Et$_3$N, CH$_4$Cl$_2$ The amino acids of Formula 1, Scheme 1 are either commercially available (eg. Aldrich Chemical Co., Milwaukee, Wis.) or may be prepared from commercially available amino acids by appropriate functional group manipulations by standard methods known to those skilled in the art.

With appropriate manipulation and protection of any chemical functionality, synthesis of the remaining compounds of the present invention is accomplished by methods analogous to those above and to those described in the Experimental section.

In order to use a compound of the present invention or a pharmaceutically acceptable salt thereof for the treatment of humans and other mammals it is normally formulated in accordance with standard pharmaceutical practice as a pharmaceutical composition.

As used herein, "treatment" of a disease includes, but is not limited to prevention, retardation and prophylaxis of the disease.

The present compounds are useful for the treatment of diseases including but not limited to bronchial asthma, allergic rhinitis, nasal polyposis, eczema, conjunctivitis, atopic dermatitis, pruritis and inflammatory bowel disease.

Compounds of the present invention and their pharmaceutically acceptable salts may be administered in a standard manner for the treatment of the indicated diseases, for example orally, parenterally, sub-lingually, dermally, transdermally, rectally, via inhalation or via buccal administration.

Compositions of the present compounds and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a present compound or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1mg to 100 mg/Kg, and each dosage unit for parenteral administration contains suitably from 0.1 mg to 100 mg/Kg, of a present compound or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a present compound. The daily dosage regimen for oral administration is suitably about 0.01 mg/Kg to 40 mg/Kg, of a present compound or a pharmaceutically acceptable salt thereof calculated as the free acid, the daily dosage regimen for parenteral administration is suitably about 0.001 mg/Kg to 40 mg/Kg, of a present compound or a pharmaceutically acceptable salt thereof calculated as the free acid, the daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the present compounds is demonstrated by the following tests:

Human eosinophils were purified by standard CD16 cell depletion using a Miltenyi cell separation column and a magnetic Super Macs magnet. Eosinophils which were >95% pure as assessed by DiffQuick staining and light microscopy were washed in PBS and resuspended in binding buffer (RPMI-1640+25 mM Hepes+0.1% Gelatin+0.1% sodium azide+0.008% CHAPS). Into a 96 well plate (Dynatek) 200,000 eosinophils, 0.25 nM 125I-Eotaxin (Amersham Plc), and compound of interest (1 nM to 100 uM) was added. This mixture of cells compound and ligand was allowed to incubate for 60 min at room temperature before harvesting. For harvesting, free ligand from bound ligand was separated over a Packard Unifilter-96 GFC, (cat #6005174) which had been pre-blocked with 1% polyethylenimine (Sigma Cat #P3143) and 1% Bovine Serum Albumin (BSA) for 2 hours prior to use. After drying, and sealing the plate with Topseal (Packard Topseal A Cat #6005185) 50 ul of MicroScint (Packard Microscint-20 Cat #6013621) was added to each well. Bound from free 125I-eotaxin was separated using a Packard Filtermate 196, 96-well plate harvester. To determine total and non-specific binding (NSB) three wells for each condition were set aside. For total binding and NSB, wells received all additions except compound. In addition NSB wells received 200 nM cold eotaxin (PeproTech, Rocky Hill, N.J.). Radioactivity associated with the filter was assessed in a Packard Topcount Microplate Scintillation Counter model number 49872V. Percent control binding was assessed by first subtracting the NSB from each well and then expressing the number of counts (CPM) associated with the compound treated sample as a percent of the control binding in the absence of compound addition.

Biological Assay for the Determination of the Inhibition of Intracellular Calcium Mobilization by Compounds of the Present Invention RBL-2H3 cells expressing the human CCR-3 receptor were grown in cell medium (EMEM medium with Earl's salts) containing 2mM L-Glutamine, 0.4 mg/ml G418 Sulfate from GIBCO BRL and 10% heat inactivated fetal calf serum from Hyclone Laboratories. The cells were seeded 30,000 cells,/well into 96-well black clear bottom sterile plates from Costar. The seeded plate was incubated overnight at 37° C. in 5% $CO_2$. On the day of the assay the cell medium was aspirated before addition of calcium dye loading solution consisting of: 1 mg/mL bovine serum albumin (BSA), 1.5 mM sulfinpyrazone from SIGMA and 4 uM Fluo-3 AM dye from Molecular Probes in cell medium, thereafter the 96-well plate was incubated for 1 hour at 37° C. The loading solution containing dye was then aspirated and replaced with fresh solution without dye after which the plate was incubated for a further 10 mins at 37° C.

This solution was aspirated and cells were washed with assay buffer (Kreb's Ringer Henseleit pH 7.4 containing 1 mM $CaCl_2$, 1.1 mM $MgCl_2$, 1.5 mM sulfinpyrazone and 1.0 mg/mL Gelatin) after aspirating the wash, 100 uLs of fresh assay buffer was added to all the wells and the plate was incubated for five minutes at 37° C. before transferring to the Fluorescent Imaging Plate Reader (FLIPR) instrument. The assay and data acquisition were initiated by addition of 50 uLs of sample diluted to a relevant concentration in assay buffer. After 2 mins 75 uLs of human Eotaxin, from PeproTech Inc., diluted to an appropriate concentration in assay buffer with 1 mg/mL BSA (no gelatin) was added to the plate and data was acquired fro an additional 1.5. mins. Concentration response data for compounds showing inhibition of calcium mobilization were performed in the presence of 33 nM Eotaxin to obtain the $IC_{50}$ values. $IC_{50}$ is the concentration ofd compound needed to inhibit 50% of the Eotaxin response.

Animal Model for the in vivo Evaluation of CCR-3 Antagonists
(Gonzalo, J. A. et al, *Immunity*, 1996, 4, 1.)

BALs were obtained from Guinea Pigs (±compound) 24 h after ovalbumin (OA) exposure to eotaxin administered via inhalation. The animals were euthanized by cervical dislocation and exsanguinated. The lungs were lavaged with 50 ml of DulBecco's PBS (5×10 cc), which was aspirated after a gentle chest massage. The BAL fluid was spun down and the pellet was resuspended in 0.25% NaCl to lyse residual erythrocytes. After centrifugation, the pellet was resuspended again in 0.9% NaCl. After a total cell count, slides were prepared and stained. The cells were differentiated into eosinophils, neutrophils and monocytes by counting a minimum of 200 cells and expressing the results as a percentage of total cells.

Alternatively, OA sensitized Guinea Pigs (±compound) were exposed to OA via inhalation 24 h after OA exposure and lungs were obtained as described above and assessed for eosinophil infltration.

The following examples are illustrative but not limiting of the embodiments of the present invention.

EXAMPLE 1

Preparation of (S)-ethyl-2-benzoylamino-3-(4-nitrophenyl)propionate a). (S)-Ethyl-2-amino-3-(4-nitrophenyl)propionate hydrochloride 4-Nitro-L-phenylalanine monohydrate (1.02 g, 4.47 mmol) was suspended in EtOH (20 mL) and HCl gas was bubbled into the suspension until a clear solution formed. The mixture was refluxed for 6.0 h. The reaction was cooled to room temperature and concentrated by rotary evaporation to yield the title compound as a white solid (1.23 g, 100%). MS (ES+) m/e 239 [M+H].

b). (S)-Ethyl-2-benzoylamino-3-(4-nitrophenyl) propionate (S)-Ethyl-2-amino-3-(4-nitrophenyl)propionate hydrochloride (1.23 g, 4.47 mmol) was suspended in dichloromethane (25 mL) and to this suspension was added benzoyl chloride (0.628 g, 4.47 mmol) and triethylamine (1.36 g, 13.4 mmol). The mixture was stirred overnight at room temperature under nitrogen. The crude reaction was washed with 5% HCl, water, brine, dried ($Na_2SO_4$), concentrated and purified by flash chromatography (silica gel, 2:1 hexanes:EtOAc) to afford the title compound as a white powder (0.865 g, 57%): MS(ES+) m/e 343 [M+H]; mp 99–101° C.

EXAMPLE 2

Preparation of (S)-ethyl-2-benzoylamino-3-(4hydroxyphenyl)propionate

L-Tyrosine ethyl ester (0.28 g, 1.35 mmol) was dissolved in DMF (9 mL). Benzoic acid (1 eq, 1.35 mmol, 0.17 g) was added, followed by N-methylmorpholine (3 eq, 4.06 mmol, 0.45 mL), 1-hydroxybenzotriazole hydrate (1.2 eq, 1.62 mmol, 0.22 g), and 1-(3-dimethylaminopropyl)-3-ethylcarbodiimide (1.2 eq, 1.62 mmol, 0.31 g). The yellow solution was allowed to stir at room temperature under nitrogen for three days. The DMF was then removed by rotary evaporation and the resulting residue partitioned between ethyl acetate and water. The organic portion was separated and washed 3×H$_2$O and 1×aq. saturated NaHCO$_3$. It was dried over MgSO$_4$, filtered, and concentrated to an oil. Trituration with diethyl ether induced formation of a white powder (0.32 g, 76%). MS (ES+) m/e 314 [M+H]$^+$, 627.

EXAMPLE 3

(S)Ethyl-2-carboxybenzoylamino-3-(4-hydroxyphenyl)propionate

L-Tyrosine ethyl ester (0.418 g, 2.0 mmol) was suspended in dichloromethane (20 mL) and to this suspension was added carboxybenzoyl chloride (0.341 g, 2.0 mmol) The mixture was stirred overnight at room temperature under nitrogen, The reaction mixture was concentrated and purified by flash chromatography (silica gel, 6:5 hexanes:EtOAc) to afford the title compound as a colorless oil (0.082 g, 16%): MS (ES+) m/e 344 [M+H].

EXAMPLE 4

(S)-Ethyl-2-benzoylamino-3-(4-methoxyphenyl)propionate

N-Benzoyl-L-tyrosine ethyl ester (0.054 g, 0.17 mmol) was dissolved in DMF (1 mL). K$_2$CO$_3$ (1 eq, 0.17 mmol, 0.024g) was added, followed by methyl iodide (1 eq, 0.17 mmol, 0.011 mL). The slightly cloudy mixture was allowed to stir at room temperature under nitrogen for 3.5 hours. An additional 2 eq K$_2$CO$_3$ was added and the mixture was allowed to stir overnight. Water was poured into the flask, causing cloudiness. Precipitation was completed via refrigeration. The resulting white solid was filtered, washed well with water and dried in air (0.030 g, 54%).

MS (ES+) m/e 328 [M+H]$^+$, 350

EXAMPLE 5

(S)-Ethyl-2-tert-butyloxycarbonylamino-3-(4-nitrophenyl)propionate

4-Nitrophenylalanine ethyl ester hydrochloride (5.21 g, 19.0 mmol) was dissolved in 2:1 THF:H$_2$O (32 mL) and cooled to 5° C. 2.5 N NaOH (1 eq, 19.0 mmol, 7.6 mL) was added, followed by di-tert-butyldicarbonate (1.1 eq, 20.9 mmol, 4.55 g). The bright yellow solution was allowed to stir at this temperature for approximately 3 hours. The solution was then poured into 0.01 N HCl and extracted 2×EtOAc. The organic portion was dried over MgSO$_4$, filtered, and concentrated to a yellow oil (6.42 g, 100%).

MS (ES+) m/e 339 [M+H]$^+$, 361

EXAMPLE 6

(S)-Ethyl-2-benzoylamino-3-(4-aminophenyl)propionate (S)-Ethyl-2-benzoylamino-3-(4-nitrophenyl)propionate (0.542 g, 1.58 mmol) was dissolved with warming in EtOH (20 mL) and to the cooled solution was added 10% Pd/C (0.108 g, 20% w/w). The mixture was stirred overnight at room temperature under a balloon of H2. The mixture was filtered through a pad of celite and the filtrate was concentrated to an off-white solid and flash chromatographed (silica gel, 1:1 hexanes:EtOAc) to afford the title compound as a white solid (0.323 g, 66%).

MS (ES+) m/e 313[M+H]; mp 120–122° C.

EXAMPLE 7

(S)-Ethyl-2-tert-butyloxycarbonylamino-3-(4-aminomethanesulfonylaminophenyl)propionate (S)-Ethyl-2-tert-butyloxycarbonylamino-3-(4-aminophenyl)propionate (0.103 g, 0.33 mmol) was dissolved in CH$_2$Cl$_2$ (1 mL) in a two-necked flask fitted with a thermometer and nitrogen line. The flask was cooled to 0° C. and pyridine (1.1 eq, 0.36 mmol, 0.030 mL) was added via syringe. Methanesulfonyl chloride (1.1 eq, 0.36 mmol, 0.028 mL) was then added dropwise at such a rate as to maintain the temperature <10° C. After addition was complete, the ice bath was removed and the bright yellow solution was allowed to warm to room temperature, turning bright orange and then pink in color as it stirred over the next two hours. The solution was poured into 1 M aqueous CuSO$_4$ and the organic portion was separated. It was washed once again with aqueous CuSO$_4$, then dried over MgSO$_4$, filtered, and concentrated to a colorless oil (0.11 g, 84%).

MS (ES+) m/e 409 [M+Na]$^+$, 450

EXAMPLE 8

(S)-Ethyl-2-tert-butyloxycarbonylamino-3-(4-acetamidophenyl)propionate (S)-Ethyl-2-tert-butyloxycarbonylamino-3-(4-aminophenyl)propionate (0.10 g, 0.31 mmol) was dissolved in ethyl acetate (4 mL). Acetic anhydride (1 eq, 0.31 mmol, 0.030 mL) was added and the pale peach solution was heated to reflux, stirring at this temperature for 6.5 hours. The heating bath was removed and the flask allowed to cool to room temperature overnight. The solution was then poured into aqueous saturated NaHCO$_3$ and extracted. The organic portion was washed again with sat. NaHCO$_3$, then it was dried over MgSO$_4$, filtered, and concentrated. Trituration with diethyl ether induced precipitation of a pale pink solid (0.09 g, 84%).

MS (ES+) m/e 351 [M+H]$^+$, 373

EXAMPLE 9

(S)-Ethyl-2-benzoylamino-3-(3,5-diiodo-4-hydroxyphenyl)propionate

Bis(pyridine)iodonium(I) tetrafluoroborate (*J. Org. Chem.*, 1990, 55,3104) (0.24 g, 0.64 mmol) was taken up in CH$_2$Cl$_2$ (3.5 mL). N-Benzoyl-L-tyrosine ethyl ester (0.5 eq, 0.32 mmol, 0.10 g) was then added, immediately causing the color of the solution to turn from pale pink to pale yellow. The solution was allowed to stir at room temperature under nitrogen for one hour. Aqueous saturated Na$_2$S$_2$O$_3$ was poured into the flask and the product extracted with CH$_2$Cl$_2$. The organic portion was dried over MgSO$_4$, filtered, and concentrated to a thin yellow oil. Trituration with diethyl ether induced precipitation of a white solid (0.11 g, 61%) which was filtered, washed well with diethyl ether and dried.

MS (ES+) m/e 566 [M+H]$^+$, 588

Preparation of Amino Acid Ethyl Esters

EXAMPLE 10

(S)-Ethyl-2-amino-3-(4-methanesulfonylaminophenyl)propionate hydrochloride (S)-Ethyl-2-tert-butyloxycarbonylamino-3-(4-methanesulfonylaminophenyl)propionate (3.00 g, 7.76 mmol) was dissolved in a solution of 4 N HCl in dioxane (10 mL). The bright orange solution was allowed to stir at room temperature overnight. The solvent was then evaporated and the residue azeotroped with toluene, furnishing the product as a bright peach solid (2.5 g, 100%).

MS (ES+) m/e 287 [M+H]$^+$, 328

EXAMPLE 11

(S)-Ethyl-2-amino-3-(4-chlorophenyl)propionate hydrochloride

The title compound was prepared using the procedure of Example 1a except substituting 4-chloro-L-phenylalanine for 4-nitro-L-phenylalanine monohydrate. White solid; MS (ES+) m/e 228 [M]$^+$, 230 [M+2]$^+$, 269, 271

EXAMPLE 12

(±)-Ethyl-2-amino-3-(3,5-(bistrifluoromethyl)phenyl)propionate hydrochloride The title compound was prepared using the procedure of Example 1a except substituting (±)-4-(3,5-bistrifluoromethyl)phenylalanine for 4-nitro-L-phenylalanine monohydrate. White solid, MS (ES+) m/e 330 [M]$^+$, 371

Formulations for pharmaceutical use incorporating compounds of the present invention can be prepared in various forms and with numerous excipients. Examples of such formulations are given below.

EXAMPLE 13

Inhalant Formulation

A present compound, (1 mg to 100 mg) is aerosolized from a metered dose inhaler to deliver the desired amount of drug per use.

EXAMPLE 14

Tablet Formulation

| Tablets/Ingredients | Per Tablet |
| --- | --- |
| 1. Active ingredient (Cpd. of Form. I or II) | 40 mg |
| 2. Corn Starch | 20 mg |
| 3. Alginic acid | 20 mg |
| 4. Sodium Alginate | 20 mg |
| 5. Mg stearate | 1.3 mg |

Procedure for Tablet Formulation

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 15

Parenteral Formulation

A pharmaceutical composition for parenteral administration is prepared by dissolving an appropriate amount of a compound of Formula I or II in polyethylene glycol with heating. This solution is then diluted with water for injections Ph Eur. (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A method of antagonizing a CCR-3 receptor by administering a compound selected from Formula (I) or Formula (II) hereinbelow:

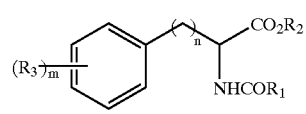

Formula (I)

wherein n is an integer from 0 to 3;

$R_1$ is selected from the group consisting of N-carbobenzoxy-L-Phe, N-Ac-L-Pro, $C_{1-6}$ alkyl, $OC_{1-4}$ alkyl, aryl and heteroaryl, unsubstituted, monosubstituted, disubstitututed or trisubstituted, with any substituents being independently selected from the group consisting of $C_{1-4}$ alkyl, COaryl, $OCH_2O$, $NO_2$, Cl and $OCH_3$.

$R_2$ represents $C_{1-4}$ alkyl or benzyl;

m is an integer from 1 to 3; and $R_3$ is independently selected from the group consisting of OH, $OC_{1-4}$ alkyl, $NO_2$, $NH_2$, halo, naphthyl, and OCOphenyl; or

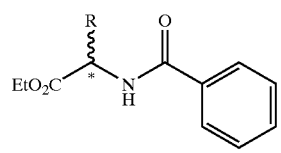

Formula (II)

wherein R represents indolylmethyl, phenyl or $(CH_2)_2$ phenyl.

2. A method according to claim 1 wherein the compound is according to Formula(II) and the carbon atom marked with the asterix (*) represents an S configuration.

3. A method according to claim 1 wherein the compound is according to Formula(I);

n represents 1; and at the $R_1$ position:

alkyl represents $cC_6H_{11}$ or n-Bu;

O-alkyl represents O-t-Bu; aryl represents phenyl or naphthyl;

heteroaryl represents thienyl, furyl, pyridyl, or quinolinyl; and any substituents at $R_1$ are independently selected from the group consisting of $C_{1-2}$ alkyl, CO-phenyl, $OCH_2O$, $NO_2$, Cl, OH, and $OCH_3$.

4. A compound according to claim 3 wherein alkyl moieties at $R_2$ are methyl or ethyl and halo moieties at $R_3$ are iodo.

5. A method according to claim 1 wherein the compound is selected from the group consisting of:

(S)-Ethyl-2-(1-napthoylamino)3-(4-nitrophenyl)propionate, (S)-Isopropyl-2-(1-napthoylamino)3-(4-nitrophenyl)propionate, (S)-Methyl-2-(1-napthoylamino)3-(4-nitrophenyl)propionate, (S)-Benzyl-2-( 1-napthoylamino)3-(4-nitrophenyl)propionate, (S)-Ethyl-2-(1-napthoylamino)3-(4-chlorophenyl)propionate, (S)-Ethyl-2-benzoylamino-3-(4-hydroxyphenyl)propionate, (S,S)-Ethyl-2-(2-benzyloxycarbonylamino-3-phenylpropionylamino)-3-(4-hydroxyphenyl)propionate,
(S,S)-Ethyl-2-(N-acetylpyrrolidine-2-benzoylamino)-3-(4-hydroxy-phenyl)propionate,
(S)-Ethyl-2-cyclohexanylamino-3-(4-hydroxyphenyl) propionate,
(S)-Ethyl-2-(3,3-diphenylpropionylamino)-3-(4-hydroxyphenyl)propionate,
(S)-Ethyl-2-(3-phenylpropionylamino)-3-(4-hydroxyphenyl)propionate,
(S)-Ethyl-2-[2-(2-naphthyl)acetylamino)-3-(4-hydroxyphenyl)propionate,
(S)-Ethyl-2-(4-phenylbutyrylamino)-3-(4hydroxyphenyl) propionate,
(S)-Ethyl-2-pentanylamino-3-(4-hydroxyphenyl) propionate,
(S)-Ethyl-2-pentanylamino-3-(4hydroxyphenyl)propionate,
(S)-Ethyl-2-(4-benzoylbenzoylamino)-3-(4-hydroxyphenyl) propionate,
(S)-Ethyl-2-(2-furanyl)amino-3-(4-hydroxyphenyl) propionate,
(S)-Ethyl-2-(1-naphthoylamino)-3-(4-hydroxyphenyl) propionate,
(S)-Ethyl-2-(5-hydroxyindonyl)amino-3-(4-hydroxyphenyl) propionate,
(S)-Ethyl-2-piperonylamino-3-( 4-hydroxyphenyl) propionate,
(S)-Ethyl-2-picolinylamino-3-(4-hydroxyphenyl) propionate,
(S)-Ethyl-2-(3-nitro-4-chlorobenzoylamino)-3-(4-hydroxyphenyl)propionate,
(S)-Ethyl-2-(3-hydroxy-4-nitrobenzoylamino)-3-(4-hydroxyphenyl)propionate,
(S)-Ethyl-2-(8-quinolinylamino)-3-(4-hydroxyphenyl) propionate,
(S)-Ethyl-2-benzoylamino-3-phenylpropionate,
(S)-Methyl-2-benzoylamino-3-(4-hydroxyphenyl) propionate,
(S)-Benzyl-2-benzoylamino-3-(4-hydroxyphenyl) propionate,
(S)-Ethyl-2-benzoylamino-3-(4-methoxyphenyl)propionate,
(S)-Ethyl-2-tert-butyloxycarbonylamino-3-(4-nitrophenyl) propionate,
(S)-Ethyl-2-tert-butyloxycarbonylamino-3-(4-aminophenyl) propionate,
(S)-Ethyl-2-benzoylamino-3-(3,5-diiodo-4-hydroxyphenyl) propionate,
(S)-Ethyl-2-carboxybenzoylamino-3-(4-hydroxyphenyl) propionate,
(S)-Ethyl-2-benzoylamino3-(1-naphthyl)propionate,
(±)-Ethyl-2-benzolyamino-3-[3-(benzoyloxy)phenyl] propionate,
(±)-Ethyl-2-benzoylamino-3-(3-hydroxyphenyl)propionate,
(R,S)-Ethyl-2-benzoylamino-3-(2-hydroxylphenyl) propionate,
(S)-Ethyl-2-benzoylamino-3-(4-aminophenyl)propionate,
(S)-Ethyl-2-benzoylamino-3-(4-nitrophenyl)propionate,
(S)-Ethyl-2-(2-phenylacetylamino)-3-(4-hydroxyphenyl) propionate,
(S)-Ethyl-2-benzoylamino-3-(3-indoyl)propionate,
(±)-Ethyl-2-(benzoylamino)-2-phenylacetate, and
(±)-Ethyl-2-(benzoylamino)-4-phenylbutyrate.

6. A method according to claim 5 wherein the compound is selected from the group consisting of:

(S)-Ethyl-2-(1-napthoylamino)3-(4-nitrophenyl)propionate,
(S)Ethyl-2-benzoylamino-3-(4-hydroxyphenyl)propionate,
(S)-Ethyl-2-cyclohexanylamino-3-(4-hydroxyphenyl) propionate,
(S)-Ethyl-2-(1-naphthoylamino)-3-(4-hydroxyphenyl) propionate,
(S)-Benzyl-2-benzoylamino-3-(4-hydroxyphenyl) propionate,
(S)-Ethyl-2-benzoylamino-3-(4-methoxyphenyl)propionate,
(S)-Ethyl-2-benzoylamino-3-(1-naphthyl)propionate,
(±)-Ethyl-2-benzolyamino-3-[3-(benzoyloxy)phenyl] propionate,
(±)-Ethyl-2-benzoylamino-3-(3-hydroxyphenyl)propionate,
(R,S)-Ethyl-2-benzoylamino-3-(2-hydroxylphenyl) propionate,
(S)-Ethyl-2-benzoylamino-3-(4-nitrophenyl)propionate,
(±)-Ethyl-2-(benzoylamino)-2-phenylacetate, and
(±)-Ethyl-2-(benzoylamino)-4-phenylbutyrate.

7. A method according to claim 6 wherein the compound is selected from the group consisting of:

(S)-Ethyl-2-(1-napthoylamino)3-(4-nitrophenyl)propionate,
(S)-Ethyl-2-(1-naphthoylamino)-3-(4-hydroxyphenyl) propionate, and
(S)-Ethyl-2-benzoylamino-3-(4-nitrophenyl)propionate.

8. A method of treating an allergic disease comprising administering to a patient in need of treatment a safe and effective amount of a compound according to Formula (I) or (II) below:

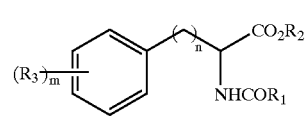

Formula (I)

wherein n is an integer from 0 to 3;

$R_1$ is selected from the group consisting of N-carbobenzoxy-L-Phe, N-Ac-L-Pro, $C_{1-6}$ alkyl, $OC_{1-4}$ alkyl, aryl and heteroaryl, unsubstituted, monosubstituted, disubstitututed or trisubstituted, with any substituents being independently selected from the group consisting of $C_{1-4}$ alkyl, COaryl, $OCH_2O$, $NO_2$, Cl and $OCH_3$.

$R_2$ represents $C_{1-4}$ alkyl or benzyl;

m is an integer from 1 to 3; and $R_3$ is independently selected from the group consisting of OH, $OC_{1-4}$ alkyl, $NO_2$, $NH_2$, halo, naphthyl, and OCOphenyl; or

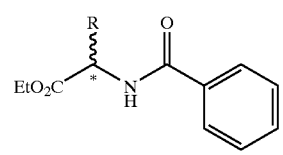

Formula (II)

wherein R represents indolylmethyl, phenyl or $(CH_2)_2$ phenyl.

9. A method according to claim 8 wherein the disease is selected from the group consisting of bronchial asthma, conjunctivitis, IBD, eczema, allergic rhinitis, nasal polyposis, atopic dermatitis, pruritis and inflammatory bowel disease.

* * * * *